(12) United States Patent
Rush et al.

(10) Patent No.: US 12,702,431 B2
(45) Date of Patent: Aug. 11, 2026

(54) INDEPENDENT SURGICAL SCREW PLACEMENT SYSTEM WITH AIMING JIG

(71) Applicant: GLOBUS MEDICAL, INC., Audubon, PA (US)

(72) Inventors: Jesse Rush, Wayne, PA (US); Richard Scheinfield, Philadelphia, PA (US); Garret Norton, Phoenixville, PA (US); Jessica Sandoe, Lansdale, PA (US)

(73) Assignee: Globus Medical, Inc., Audubon, PA (US)

( * ) Notice: Subject to any disclaimer, the term of this patent is extended or adjusted under 35 U.S.C. 154(b) by 0 days.

(21) Appl. No.: 18/922,745

(22) Filed: Oct. 22, 2024

(65) Prior Publication Data

US 2026/0108261 A1 Apr. 23, 2026

(51) Int. Cl.

| | |
|---|---|
| ***A61B 17/17*** | (2006.01) |
| ***A61B 17/80*** | (2006.01) |
| ***A61B 17/90*** | (2006.01) |
| *A61B 17/00* | (2006.01) |

(52) U.S. Cl.

CPC ...... *A61B 17/1775* (2016.11); *A61B 17/1728* (2013.01); *A61B 17/8061* (2013.01); *A61B 17/808* (2013.01); *A61B 17/90* (2021.08); *A61B 2017/00991* (2013.01)

(58) Field of Classification Search

CPC ............ A61B 17/1725; A61B 17/1728; A61B 17/1775; A61B 17/8061; A61B 17/808; A61B 17/90

See application file for complete search history.

(56) References Cited

U.S. PATENT DOCUMENTS

| | | | | |
|---|---|---|---|---|
| 9,204,912 | B2 * | 12/2015 | Price .................. | A61B 17/8057 |
| 10,201,358 | B2 | 2/2019 | Seykora et al. | |
| 10,799,276 | B2 | 10/2020 | Dacosta et al. | |
| 11,123,120 | B2 * | 9/2021 | Dacosta ............. | A61B 17/8061 |
| 11,622,778 | B2 * | 4/2023 | Leither .............. | A61B 17/1728 606/96 |
| 11,925,364 | B2 | 3/2024 | Dacosta et al. | |
| 2014/0180348 | A1 * | 6/2014 | Thoren .................. | A61B 17/17 606/86 R |
| 2021/0052308 | A1 | 2/2021 | Thoren et al. | |
| 2023/0081410 | A1 * | 3/2023 | Peterson ............ | A61B 17/1782 606/62 |

FOREIGN PATENT DOCUMENTS

| | | | |
|---|---|---|---|
| CN | 114795445 | A | 7/2022 |
| WO | 2022136287 | A1 | 6/2022 |

* cited by examiner

*Primary Examiner* — Larry E Waggle, Jr.

(57) ABSTRACT

An independent, surgical screw placement system makes use of an aiming jig. The aiming jig has components and features which can be suitably adjusted so that an independent or extra-plate screw avoids crossing the nominal trajectories of other joint screws securing a surgical plate to a foot in an associated surgery. The aiming jig has a telescoping arm which can be adjusted to a variety of potential trajectories for the independent surgical screw until a desired trajectory for such independent screw has been determined.

11 Claims, 3 Drawing Sheets

L
49
91
21
53
33
57
85
45
45
α
77
51
39
81
25
39
43
61
92
37
R
29
47
83
23
89
27
29

33
79
49
91
81
45
21
51
57
92
63
43
75
76
65
5
61
73
47
71
5

INDEPENDENT SURGICAL SCREW PLACEMENT SYSTEM WITH AIMING JIG

FIELD

This disclosure relates to systems and apparatus associated with orthopedic surgical procedures, in general, and to systems for placing screws related to surgical plates associated with such surgical procedures, in particular.

BACKGROUND

Various surgical procedures relating to foot joints, including the Lisfranc joint and the first tarsometatarsal (TMT) joint, often make use of independent or extraplate screws which are placed outside of the associated plates and their associated joint screws. One of the challenges in placing such an independent screw outside of an associated plate involves avoiding joint screws which are to be placed or already placed through the associated plate. It would be desirable to have surgical systems and associated methods to improve the placement of independent screws in connection with orthopedic surgeries.

SUMMARY

In one suitable implementation, this disclosure relates to an independent, surgical screw placement system, such as for a surgical procedure on a foot joint. The system first includes a suitable surgical plate sized to extend over the joint in question, such as a foot joint. As such, the surgical plate has upper and lower surfaces, as well as multiple screw holes located to allow the plate to be secured by plate or joint screws to an adjacent bone, joint, or combination of the foregoing.

Multiple joint screws are advanceable into the foregoing screw holes to be secured to the foot joint at corresponding joint locations. In this disclosure, the joint screws define respective, nominal trajectories, such as in the foot joint, and the system has features to permit an independent surgical screw to be placed outside of the plate and without crossing the nominal trajectories of the joint screw. The desired placement of the independent screw is accomplished with the assistance of an aiming jig, which aiming jig is removably securable to the plate.

In certain implementations, the independent surgical screw placement system makes use of a connector which is located between the aforementioned plate and the aiming jig. The connector may be equipped with features which key or fix the angular orientation of the aiming jig relative to the plate for purposes of subsequently assisting in the desired, non-interfering placement of the independent surgical screw. By way of example, certain implementations may have the connector in the form of a pilot pin mateable with an opposing pilot hole. A threadable connection can be operated to secure the aiming jig relative to the plate upon mating of the pilot pin and the pilot hole.

In still further implementations, the aiming jig includes an arm. One end of the arm is located near the plate. The arm extends from this first end upwardly, that is, in a superior direction, from the plate, and then either medially or laterally, depending on the desired trajectory for the independent screw, to terminate in a second end. The second end of the arm is thus at a spaced location relative to the plate. A housing is secured at the second end of the aiming jig. The threadable connection of the connector is, for its part, disposed at the opposite, first end of the arm.

The aiming jig has features which may be adjusted by the user to create a user determined trajectory for the independent screw, preferably a trajectory that does not cross the nominal trajectories of any joint screws. To that end, the arm may include first and second telescoping portions which can be selectively movable and fixable to locate the housing at a user-selected angle relative to the plate. Such user-selected angle is one of the parameters of the user-determined trajectory of the independent screw.

According to still further implementations, the housing includes three housing apertures, each extending between opposite proximal and distal sides. The proximal side is accessible by the surgeon or other user, and the distal side is located in operative proximity to the joint undergoing the procedure, such as one of the foot joints.

A k-wire tube is likewise part of the above-described surgical placement system and can be placed in any one of the apertures of the housing. The apertures have respective central axes, and are oriented to define a convergence point which corresponds to the distal end of an independent screw potentially insertable along the user-determined trajectory.

BRIEF DESCRIPTION OF THE DRAWINGS

The foregoing implementations and their features will be better understood with reference to the description herein and the drawings, in which.

DETAILED DESCRIPTION

Referring to FIGS. 1-6, in one suitable implementation according to the present disclosure, an independent, surgical screw placement system 21 is suitable for use with a variety of orthopedic, surgical procedures in general, and for surgical procedures related to the foot. In the illustrated implementations herein, this system 21 is shown relative to foot joint j in connection with a surgical procedure associated therewith, such as repair of a Lisfranc injury. System 21 may be used in any number of other procedures involving surgical plates, whether for the foot or elsewhere, such as with a Lapidus procedure.

Figures 1, 2:
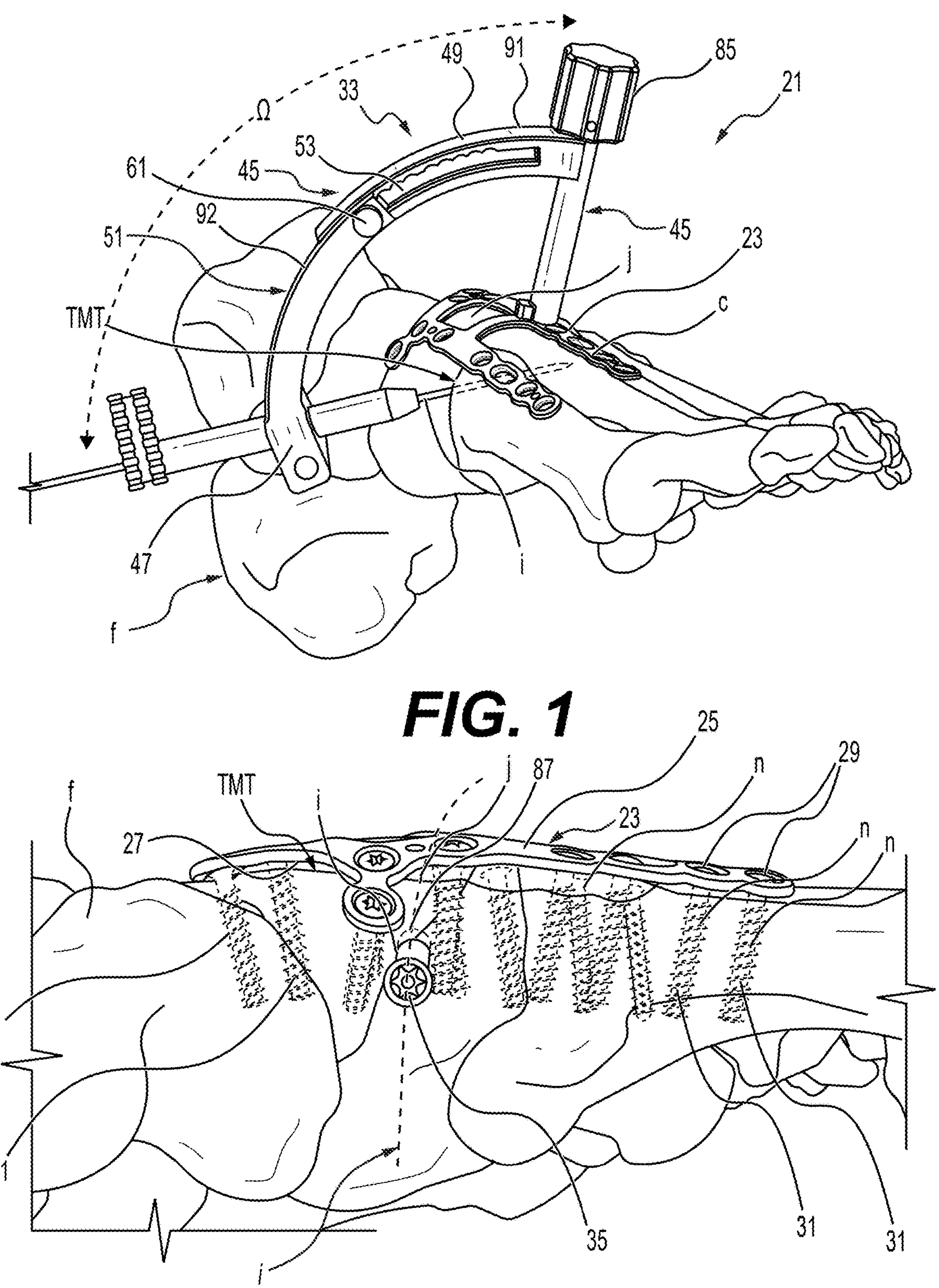
FIG. 1 is a perspective view of an independent, surgical screw placement system shown relative to a foot joint undergoing a surgical procedure.
FIG. 2 is a partial side elevational view showing a plurality of joint screws and corresponding nominal trajectories in a foot joint, and an independent screw avoiding such nominal trajectories.

In the implementation illustrated in FIGS. 1-2, a surgical plate 23 is sized to extend over foot joint j, plate 23 having upper and lower surfaces 25, 27 formed thereon, and operatively connectable to foot joint j. Plate 23 has a plurality of screw holes 29 extending through surfaces 25, 27 at spaced locations on plate 23. As shown in FIG. 2, a plurality of joint screws 31 are adapted to be received in screw holes 29 and secured to foot joint j at corresponding joint locations. Screw holes 29 and screws 31 define nominal trajectories n, meaning joint screws 31 extend through associated screw holes 29 along trajectories within a standard deviation. As such, joint screws 31 are advanced through screw holes 29 into foot joint j with trajectories that may vary from being strictly orthogonal relative to plate 23 and thus include various trajectories through foot joint j, all of which are considered nominal so long as they pass through screw holes 29.

Surgical screw placement system 21 makes use of an aiming jig 23 which is removably securable to plate 23 and adapted to be oriented to permit advancing of an independent or extraplate screw 35. Aiming jig 23 can be adjusted to a user-selectable orientation that does not cross the nominal trajectory n of joint screws 31. Aiming jig 33 may be removably secured to plate 23 before or during surgical procedures in any number of suitable ways. In the illustrated implementation, a connector 37 for such purpose is disposed between plate 23 and jig 33. Connector 37 is keyed to allow the user to fix one of the parameters of the orientation of aiming jig 33. Still other parameters of orientation of aiming jig 33, as well as the orientation of a user-selectable trajectory for independent screw 35, are described subsequently herein.

Connector 37 makes use of a pilot pin 39 which is mateable with an opposing pilot hole 41 and secured by means of a threadable connection 43. In this matter, aiming jig 33 is secured upon mating pilot pin 39 and pilot hole 41.

Aiming jig 33 includes an arm 45 which has a first end located proximate to plate 23, which arm 45 extends from plate 23 to a second end where a housing 47 is disposed. Threadable connection 43 is disposed at the first end of arm 45 and connected to plate 23.

Arm 45 includes two telescoping portions 49, 51 which vary the overall length of arm 45 as well as adjusting potential trajectories for independent screw 35 which may be selected by a surgeon or other medical professional. First telescoping portion 49 includes a rail 53 with a slot 55 defined therein. Second telescoping portion 51 comprises a tongue 57. Tongue 57 is selectively slidable and engageable with detents 59 formed in slot 55 of first telescoping portion 49. Button 61 is suitably interconnected between the first and second telescoping portions 49, 51 to permit selective telescoping of the portions relative to each other, and to fix such portions at a desired extension or contraction with corresponding lengths associated with the various positions of detents 59.

User-selectable trajectory i of independent screw 35 may be characterized by multiple angular, parameters relative to surgical plate 23. One such angular parameter is the user-selectable angle which can be created by selectively moving and thereby fixing the telescoping arm portions 49, 51 relative to each other. One such user-selectable angle shown as angle Ω relative to plate 23 (FIG. 1). In one suitable implantation, user-actuatable button 61 may be spring biased to a first position engaging a selected one of detents 59, thereby fixing telescoping portions 49, 51 relative to each other, including tongue 57 relative to rail 53. To adjust the user-selectable trajectory i for independent screw 37 to a new angular trajectory, button 61 may be actuated to overcome any spring bias, such that a suitable engaging portion of button 61 disengages from the previously engaged detent 59, and permits telescoping inwardly or outwardly of telescoping portions 49, 51 relative to each other, thereby establishing another user-selectable angle Ω with a different angular value relative to plate 23. The adjustment process of the user-selectable trajectory for independent screw 35, including adjusting the parameter of the user-selected angle Ω formed by arm 45 relative to plate 23, may be repeated until the user selects an angular trajectory i and corresponding selectable angle Ω which will avoid crossing the nominal trajectories n of joint screws 31. In the illustrated implementations, telescoping portions 49, 51 are in the form of arcs or arcuate portions. When arm 45 is connected to plate 23, such arcuate portions extend medially from connector 37.

Housing 47 has distal and proximal sides, that is, distal side located to be opposing and in operative proximity to foot f and the foot joint j undergoing the associated surgical procedure. The proximal side, as shown, is located opposite the distal side and, as such, is accessible by the user during the associated procedure. Housing 47 has formed therein at least one housing aperture 63 extending through the proximal and distal sides. In the illustrated implementation, there are three of the housing apertures 63 configured for further user-selectable adjustments as described subsequently.

Aiming jig 33 includes a suitably sized k-wire tube 65 which is able to be received through one or more of housing apertures 63 and selectively removable therefrom after associated operations have been completed. As such, k-wire tube 71 is sized to have a longitudinally extending k-wire bore 67 capable of receiving an appropriately sized k-wire therethrough. As such, k-wire tube 65 is selectively slidable by a user, such as a surgeon, both proximally and distally to a desired position relative to housing 47.

Aiming jig 33 includes a locking mechanism 69 to fix such user-selectable position of k-wire tube 65 at the desired position. In the illustrated implementation, locking mechanism 69 makes use of a longitudinally extending cut-out 71 (FIG. 5) formed in k-wire tube 65 in its outside surface. Cut-out 71 interfaces with a shoulder 73 which has been defined in the k-wire bore 67. Cut-out 71 and shoulder 73 are selectively brought into engagement or disengagement in an interference fit by means of a user accessible handle 75 connected to k-wire tube 65. Rotation of handle 75 causes rotation of cut-out 71 within k-wire bore 67 and relative to shoulder 73. The rotated position of handle 75 may be user observable by equipping or configuring handle 75 with a handle portion 76, such as an indicator, lever, or tail (as shown), or by a suitable indicia showing locked or unlocked position of k-wire tube 65 within housing aperture 63.

Figures 5, 6:
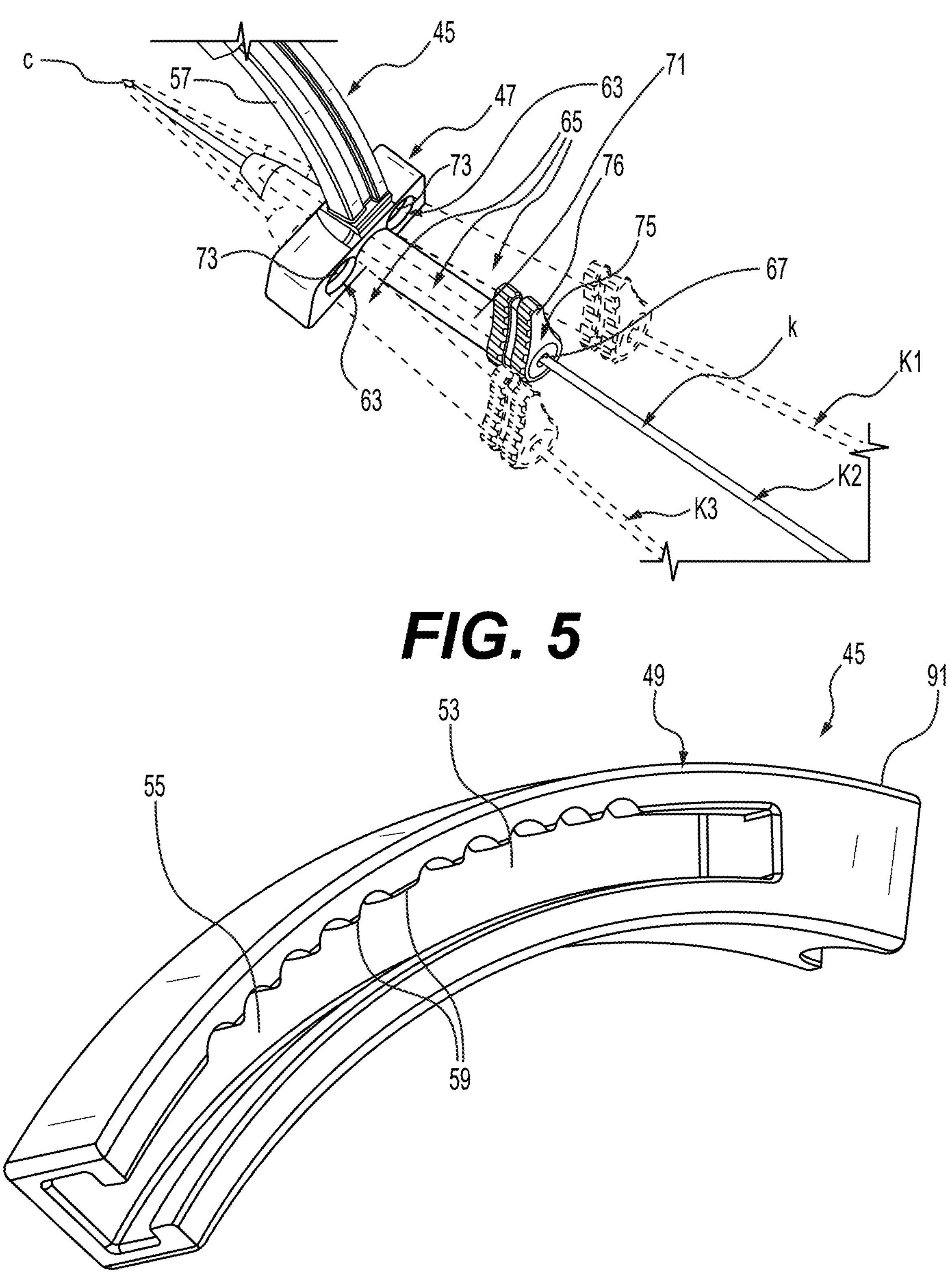
FIG. 5 is a perspective view of one portion of the independent, surgical screw placement system of FIGS. 3-4 taken along line 5-5 of FIG. 4.
FIG. 6 is an enlarged, perspective view of one of the components of the arm of the independent, surgical screw placement systems of FIGS. 3-5.

As seen in FIG. 5, the three apertures 63 of housing 47 have respective central longitudinal axes K1, K2, K3 angled relative to each other to define a convergence point c spaced from housing 47 distally. Arm 45 and its telescoping portions 49, 51 permit housing 47 to be located relative to foot joint j so that convergence point c corresponds to a distal end 87 of independent screw 37 after insertion thereof into foot joint j as a result of the corresponding surgical procedure.

Figures 3, 4:
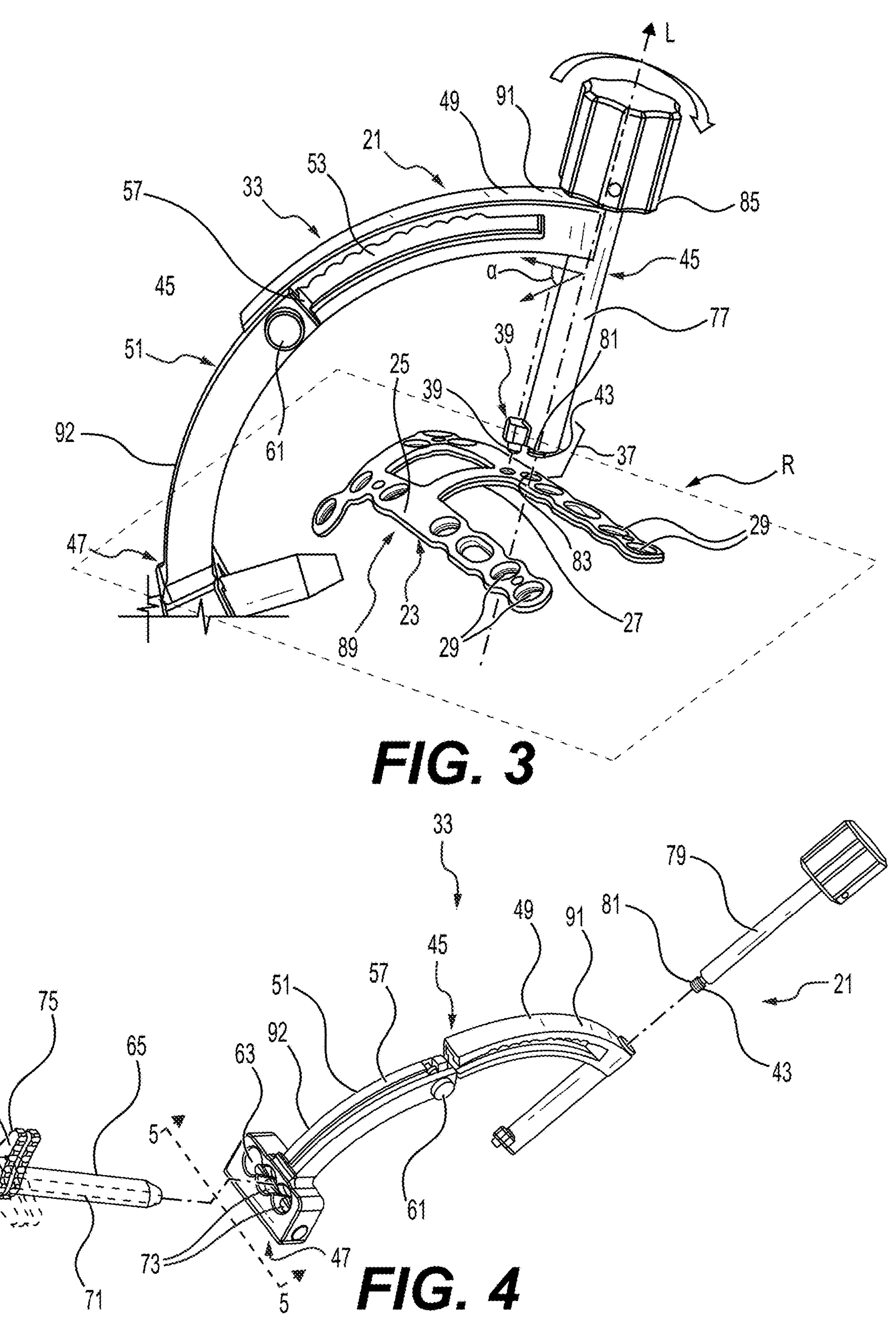
FIG. 3 is a partially exploded, perspective view of an implementation of an independent, surgical screw placement system.
FIG. 4 is a further exploded view of the independent, surgical screw placement system of FIG. 3.

In one suitable implementation, such that shown in FIGS. 1-3, surgical plate 23 comprises a dorsal plate 89 adapted to be secured to and extend over a first tarsometatarsal joint (TMT) in association with a Lisfranc injury repair procedure, for example. Dorsal plate 89 has a distal surface capable of being brought against foot joint j during the associated surgical procedure, and a proximal surface opposite the distal surface which is adapted to face away, that is, in the superior direction, from foot joint j when secured thereto.

When surgical screw placement system 21 is adapted for such (TMT) or Lisfranc procedures, aiming jig 33 is configured so that housing 47 is generally positioned at a spaced distance from the medial side of foot joint j. Such position allows aiming jig 33 to have one or more user-selectable trajectories originate from the medial side of foot joint j such that at least one such available trajectory may be selected as one that does not cross the nominal trajectories n of joint screws 31.

For dorsal plate 89, a plurality of screw holes 29 extend anteriorly from a posterior edge of dorsal plate 89. Aiming jig 33 is removably securable to at least one location on dorsal plate 89 which is posterior to at least one of the anteriorly extending screw holes 29.

Arm 45 of aiming jig 33 is formed with an arm tube 77 located at the end of arm 45 proximate to dorsal plate 89. A post shaft 79 is movably received within arm tube 77. Arm tube 77 and post shaft 79 have respective, proximal and distal ends extending coaxially about a longitudinal, arm-tube axis L.

Threadable connection 43 includes a threaded shaft 81 which is disposed and formed at the foregoing, distal end of post shaft 79 and extends longitudinally and distally therefrom. Mating with threaded shaft 81 is a corresponding threaded bore 83 formed at a suitable location in dorsal plate 89, such as a location posterior to multiple screw holes 29. Together, threaded shaft 81 and threaded bore 83 form the threadable connection 43.

Pilot pin 39 is disposed on the distal end of arm tube 77 and, like threaded shaft 81, pilot pin 39 extends longitudinally and distally, but from arm tube 77. Pilot hole 41 is formed on the surface of dorsal plate 89 at a corresponding location so as to receive pilot pin 39 therein, such corresponding location being adjacent to threaded bore 83 of the threadable connection 43. As illustrated, pilot pin 41 and the threaded shaft 81 extend parallel to each other, which, in turn, causes arm tube 77 to extend substantially orthogonally from dorsal plate 89 and secured thereto. Portions 49, 51, of arm 45 extend radially and arcuately outwardly from longitudinal axis L of arm tube 77 when connected to dorsal plate 89. The relative location of threaded bore 83 and pilot hole 41 in dorsal plate 89 thus determines an angular orientation Ω of arm 45 of aiming jig 33 relative to plate 89.

System 21 further comprises a user-actuatable post handle 85 connection to the proximal end of post shaft 79 so that threaded shaft 81 of post shaft 79 may be rotated and thus screwed into threaded bore 83 formed in dorsal plate 89. Telescoping portion 49 of arm 45 includes a first, arcuate portion 91, and rail 53 and slot 55 extend over such arcuate portion 91. Telescoping portion 51 of arm 45 includes a corresponding, second, arcuate portion 92, with tongue 57 and user actuatable button 61 located on such second arcuate portion 92. Such arrangement permits arm 45 to be adjusted through a range of angular positions relative to reference plane R of dorsal plate 89. In one suitable implementation, slot 55 extends sufficiently so that a range of angular positions may be selected from 60° to 120° relative to reference plane R of dorsal plate 89.

The operation of independent, surgical screw placement system 21 is apparent from the foregoing description, in connection with any number of associated workflows and surgical procedures involving surgical plates on anatomical joints, such as the TMT and other foot joints. In one suitable workflow, a process for inserting an independent surgical screw into a foot joint outside of a plate involves using the adjustable features of independent surgical screw placement system 21 to fix a first location spaced from the upper surface of the surgical plate. The fixed location is located outside of a boundary zone, which boundary zone is defined as the outer edge of the surgical plate. The first location is fixed to define a first, angular orientation relative to the plate. That first angular orientation corresponds to a first potential trajectory, or given the three, available housing apertures 63, to a set of three trajectories having a common convergence point c, such trajectory or set of trajectories available to the use for insertion of the independent screw outside the plate.

If, however, it is determined that such first potential trajectory or the set of trajectories does not avoid the nominal trajectory of all the joint screws, then such first location is adjusted by suitable manipulation of aiming jig 33 to fix a second location. This second location is also spaced from the upper surface of the plate, also outside the boundary zone defined by the plate, and defines a second, angular orientation relative to such plate.

As such, the second angular orientation corresponds to a second potential trajectory (or set of trajectories in the event of multiple, housing apertures 63) of the independent screw for insertion from outside the plate. It is then determined if such second potential trajectory (or trajectories) constitutes an available trajectory, which means a trajectory that avoids the nominal trajectories of all of the joint screws.

The foregoing adjustments to different spaced locations with corresponding angular orientations may be repeated until such time as one of the potential trajectories is, in fact, determined to constitute an available trajectory (that is, a trajectory that avoids the nominal trajectories of the joint screws). Upon such determination of an available trajectory, then the following steps may be performed: first, a k-wire is advanced along the available trajectory into the foot joint and thereafter removed therefrom. A drill may subsequently be advanced along the pathway defined by the previously inserted k-wire to form a bore sized to receive the independent screw therein. After the drill forms the appropriately sized bore, the independent screw may be advanced along the available trajectory into the bore.

As mentioned above, the three housing apertures 63 of housing 47 may be employed to make further, angular orientations available to thus provide further trajectory options in the search for an optimal, available trajectory in which the independent screw avoids the nominal trajectories for all the joint screws. For example, at any fixed position of housing 47, the angular orientation of k-wire tube shaft 65 may be adjusted between one of three different angles by inserting the tube shaft 65 into a selected one of the housing apertures of 63 (FIG. 5). Each of the three, different angular orientations shares a common convergence point corresponding to distal end of independent screw 35 upon insertion, but at least one of such three positions may avoid the nominal trajectories of the joint screws, as opposed another angular orientation of a housing aperture 63 which does not. Handle 75 of k-wire tube shaft 65 can be used to lock the k-wire tube within housing aperture 63 and may likewise permit the bore 67 of k-wire tube shaft 65 to be moved into operative proximity immediately adjacent to tissue of the foot joint being operated upon.

The k-wire tube shaft 65 and its bore 67 are sized to permit proximal and distal movement of k-wires and drills along the selected trajectory. However, tube shaft 65 and bore 67 impedes movement of the k-wire and the drill from deviating from the available trajectory once the k-wire tube shaft has been selected and fixed for the location of housing 47 which has been fixed by aiming jig 33.

After k-wire insertion and drilling, the k-wire tube shaft may be removed from the corresponding one of the housing aperture 63, and independent screw 35 may be inserted through such housing aperture to advance it into the joint outside of the plates on the trajectory which avoids crossing the nominal trajectories of the joint screws.

Among the advantages of the independent screw placement system 21 and its aiming jig 33 is that they enhance and optimize placement of an independent or extra-plate screw relative to the other joint screws associated with a surgical plate, especially a plate associated with a Lisfranc or Lapidus procedure.

As a related advantage, the adjustability of the components of aiming jig 33 allow the surgeon or other medical practitioner to account for the variability in patient anatomy.

It will be further understood that various changes in the details, materials, and arrangements of the components disclosed herein may be made by those skilled in the art without departing from the spirit and scope of the present disclosure. Furthermore, one skilled in the art would appreciate that the illustrated and disclosed embodiments and variations thereof are non-limiting. It will also be appreciated that one or more features may be omitted from one or more other alternative embodiments without departing from the scope of the disclosure as expressed in the claims appended hereto.

What is claimed is:

1. An independent, surgical screw placement system for a surgical procedure on a foot joint, the system comprising:

a surgical plate sized to extend over the foot joint, the plate having upper and lower surfaces and a plurality of screw holes extending therethrough at spaced locations on the plate;

a plurality of joint screws adapted to be received in the screw holes and secured to the foot joint at corresponding joint locations, the screws defining respective, nominal trajectories in the foot joint;

an aiming jig removably securable to the plate, the aiming jig adapted to be adjustable to a user-selectable trajectory for an independent screw that does not cross the nominal trajectories of the joint screws, wherein the aiming jig comprises an arm having a first end located at the plate, the arm extending from the plate to a second end, the second end terminating in a housing and the user-selectable trajectory of the independent screw is characterized by multiple, angular parameters relative to the plate; and a connector disposed between the plate and the aiming jig, the connector keyed to fix an angular orientation of the aiming jig relative to the plate and comprising a pilot pin mateable with an opposing pilot hole and a threadable connection disposed at the first end of the arm operable to secure the aiming jig relative to the plate upon mating of the pilot pin and the pilot hole, wherein the arm includes first and second telescoping portions, the telescoping portions located and extending between the first and second ends of the arm, the telescoping portions being selectively moveable and fixable to locate the housing at a user-selectable angle relative to the plate, the user-selectable angle constituting one of the parameters of the user-selectable trajectory of the independent screw, wherein the first telescoping portion comprises a longitudinally extending rail with a longitudinally extending slot defined therein, the second telescoping portion defining a tongue slidably received in the slot;

wherein the rail has a plurality of longitudinally spaced detents defined adjacent the slot; and wherein the tongue includes a user-actuatable button, the button having a first position engaging a selected one of the detents to fix the rail and tongue relative to each other, the button having a second position disengaged from the detents to telescope the telescoping portions relative to each other.

2. The system of claim 1, wherein the telescoping portions comprise arcuate portions extending medially from the connector.

3. The system of claim 2, wherein the rail and the slot are located on one of the arcuate portions, and wherein the tongue and the user-actuatable button are located on the other of the arcuate portions to telescope the second end of the arm through a range of angular positions relative to a reference plane of the plate;

wherein the slot extends sufficiently for the range of angular positions to extend from 60° to 120° relative to the reference plane associated with the plate.

4. The system of claim 1, wherein the housing comprises distal and proximal sides, the distal side located to be opposing and in operative proximity to a foot associated with the foot joint when undergoing the procedure, the proximal side located to be user-accessible during the procedure;

wherein the housing further comprises at least one housing aperture extending through the sides;

wherein the aiming jig further comprises a k-wire tube removably receivable through the housing aperture, the k-wire tube having a longitudinally extending k-wire bore sized to receive a k-wire therethrough.

5. The system of claim 4, wherein the k-wire tube is selectively slidable proximally and distally to a desired position relative to the housing, and wherein the aiming jig includes a locking mechanism to fix the k-wire tube at the desired position.

6. The system of claim 5;

wherein the locking mechanism comprises a longitudinally extending cut-out defined in an outer surface of the k-wire tube, the locking mechanism further including a shoulder defined in the k-wire bore, and a handle disposed at a proximal end of the k-wire tube, the handle connected to the k-wire tube so that rotation of the handle causes rotation of the cut-out within the bore relative to the shoulder;

wherein sufficient rotation of the handle relative to the shoulder selectively locks and unlocks the k-wire tube at the desired position, the handle further having a portion indicating whether the corresponding k-wire tube is in the locked or unlocked position.

7. The system of claim 4, further comprising three of the housing apertures, each of the housing apertures having respective central axes, the axes angled relative to each other to define a convergence point spaced from the housing distally, the housing locatable relative to the foot of the foot joint so that the convergence point corresponds to the distal end of the independent screw after insertion into the foot joint during the procedure.

8. The system of claim 1, wherein the surgical plate comprises a dorsal plate adapted to be secured to and extend over a first tarsometatarsal joint in association with a Lisfranc injury repair procedure, the dorsal plate having a distal surface capable of being brought against the foot joint during the procedure and a proximal surface opposite the distal surface and adapted to face away from the foot joint when secured to the foot joint;

wherein the aiming jig is adapted to locate the housing on a medial side of the foot joint and the aiming jig is adapted to have the user-selectable trajectory originate from the medial side.

9. The system of claim 8, wherein the screw holes extend anteriorly, and wherein the aiming jig is removably securable to at least one location on the dorsal plate posterior to at least one of the screw holes.

10. The system of claim 9, wherein the arm of the aiming jig comprises an arm tube at the first end of the arm and a post shaft movably received within the arm tube;

wherein the arm tube and the post shaft have respective proximal and distal ends and are co-axial about a longitudinal, arm-tube axis;

wherein the threadable connection comprises a threaded shaft disposed at the distal end of the post shaft and extending longitudinally therefrom, the threadable connection further comprising a corresponding threaded bore formed in the dorsal plate at a location posterior to multiple ones of the screw holes;

wherein the pilot pin is disposed on the distal end of the arm tube and extends longitudinally and distally from the arm tube;

wherein the pilot hole is formed on the proximal surface of the dorsal plate adjacent to the threaded bore of the threadable connection;

wherein the pilot pin and the threaded shaft extend parallel to each other, whereby the arm tube extends orthogonally from the proximal surface of the dorsal plate when secured thereto;

wherein the telescoping portions of the arm extend radially and arcuately outwardly from the arm-tube longitudinal axis when connected to the plate;

wherein the relative location of the threaded bore in the dorsal plate and the pilot hole in the dorsal plate determines an angular orientation of the arm of the aiming jig relative to the plate.

11. The system of claim 10, further comprising a user-actuatable post handle connected to the proximal end of the post shaft to screw the threaded shaft of the post shaft into the threaded bore of the plate.

* * * * *